US011783916B2

(12) United States Patent
Chang et al.

(10) Patent No.: US 11,783,916 B2
(45) Date of Patent: Oct. 10, 2023

(54) SYSTEM AND METHOD FOR ACQUISITION AND PROCESSING OF MULTIPLEXED FLUORESCENCE IN-SITU HYBRIDIZATION IMAGES

(71) Applicant: Applied Materials, Inc., Santa Clara, CA (US)

(72) Inventors: Yun-Ching Chang, San Jose, CA (US); Dan Xie, Dublin, CA (US); Chloe Kim, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 91 days.

(21) Appl. No.: 17/124,353

(22) Filed: Dec. 16, 2020

(65) Prior Publication Data

US 2021/0199584 A1    Jul. 1, 2021

Related U.S. Application Data

(60) Provisional application No. 62/949,391, filed on Dec. 17, 2019.

(51) Int. Cl.
*G06K 9/00*        (2022.01)
*G16B 40/10*       (2019.01)
(Continued)

(52) U.S. Cl.
CPC .......... *G16B 40/10* (2019.02); *C12Q 1/6841* (2013.01); *G01N 21/6428* (2013.01);
(Continued)

(58) Field of Classification Search
CPC ........ G16B 40/10; G16B 50/00; G16B 50/40; C12Q 1/6841; G01N 21/6428;
(Continued)

(56) References Cited

U.S. PATENT DOCUMENTS 7,139,415 B2  11/2006  Finkbeiner
7,826,977 B2  11/2010  Garty et al.
(Continued)

FOREIGN PATENT DOCUMENTS

JP   H06-004601   1/1994
KR   10-0437253   6/2004
(Continued)

OTHER PUBLICATIONS

International Search Report and Written Opinion in International Appln. No. PCT/US2020/014156, dated May 11, 2020, 12 pages.
(Continued)

*Primary Examiner* — Shervin K Nakhjavan
(74) *Attorney, Agent, or Firm* — Fish & Richardson P.C.

(57) ABSTRACT

In acquisition of spatial transcriptomic information, a plurality of images representing a common field of view of a sample are obtained and registered. Each pixel of the registered images is decoded by identifying a code word from a plurality of code words in a code book that provides a best match to data values in the plurality of registered images for the pixel. For each code word identified as a best match and each pixel, whether a bit ratio for an image word for the pixel meets a threshold for the code word is determined. The image word is formed from the data values in the plurality of registered images for the pixel. For at least one pixel that is determined to meet the threshold, a gene associated with the code word is determined. Pixels for which the bit ratio does not meet the threshold are screened.

18 Claims, 9 Drawing Sheets

(51) Int. Cl.
    *G02B 21/00*     (2006.01)
    *G01N 21/64*     (2006.01)
    *C12Q 1/6841*     (2018.01)
    *G02B 21/16*     (2006.01)
    *G02B 21/36*     (2006.01)
    *G06T 5/00*     (2006.01)
    *G06T 5/20*     (2006.01)
    *G06T 5/50*     (2006.01)
    *G06T 7/00*     (2017.01)
    *G16B 50/40*     (2019.01)
    *G06V 10/30*     (2022.01)
    *G06V 20/69*     (2022.01)
    *G06V 10/50*     (2022.01)
    *G06V 10/75*     (2022.01)
    *G16B 50/00*     (2019.01)
    *G01N 21/75*     (2006.01)

(52) U.S. Cl.
CPC ..... *G01N 21/6456* (2013.01); *G01N 21/6458* (2013.01); *G02B 21/0076* (2013.01); *G02B 21/16* (2013.01); *G02B 21/365* (2013.01); *G02B 21/367* (2013.01); *G06T 5/003* (2013.01); *G06T 5/006* (2013.01); *G06T 5/20* (2013.01); *G06T 5/50* (2013.01); *G06T 7/0012* (2013.01); *G06V 10/30* (2022.01); *G06V 10/507* (2022.01); *G06V 10/758* (2022.01); *G06V 20/69* (2022.01); *G06V 20/698* (2022.01); *G16B 50/00* (2019.02); *G16B 50/40* (2019.02); *G01N 2021/6419* (2013.01); *G01N 2021/6421* (2013.01); *G01N 2021/6441* (2013.01); *G01N 2021/755* (2013.01); *G01N 2201/12761* (2013.01); *G06T 2207/10056* (2013.01); *G06T 2207/10064* (2013.01); *G06T 2207/30004* (2013.01); *G06T 2207/30168* (2013.01)

(58) Field of Classification Search
CPC ........... G01N 21/6456; G01N 21/6458; G01N 2021/6419; G01N 2021/755; G01N 2201/12761; G02B 21/0076; G02B 21/16; G02B 21/365; G02B 21/367; G06T 5/003; G06T 5/006; G06T 5/20; G06T 5/50; G06T 7/0012; G06T 2207/10056; G06T 2207/10064; G06T 2207/30004; G06T 2207/30168; G06T 3/4038; G06T 2207/30204; G06T 7/0002; G06T 7/33; G06V 10/30; G06V 10/507; G06V 10/758; G06V 20/69; G06V 20/698
See application file for complete search history.

(56) References Cited

U.S. PATENT DOCUMENTS

| | | | |
|---|---|---|---|
| 8,116,543 B2 | 2/2012 | Perz et al. | |
| 9,029,159 B2 | 5/2015 | Furrer et al. | |
| 9,494,521 B2 | 11/2016 | Holmes et al. | |
| 10,664,967 B2* | 5/2020 | Barnes | G06T 7/90 |
| 2001/0036304 A1* | 11/2001 | Yang | G06F 18/40 |
| | | | 382/132 |
| 2001/0050999 A1 | 12/2001 | Bacus et al. | |
| 2003/0081209 A1 | 5/2003 | Takahashi et al. | |
| 2007/0195321 A1 | 8/2007 | Soussaline et al. | |
| 2008/0212865 A1 | 9/2008 | Zhu et al. | |
| 2008/0232658 A1* | 9/2008 | Sugaya | G06T 7/0012 |
| | | | 382/128 |
| 2010/0034444 A1* | 2/2010 | Emhoff | G06F 18/00 |
| | | | 382/129 |
| 2010/0111396 A1* | 5/2010 | Boucheron | G06F 18/29 |
| | | | 382/133 |
| 2018/0031817 A1 | 2/2018 | Barral | |
| 2018/0232883 A1 | 8/2018 | Sethi et al. | |
| 2019/0005304 A1 | 1/2019 | Adalsteinsson et al. | |
| 2019/0333199 A1* | 10/2019 | Ozcan | G06T 3/4046 |
| 2021/0199584 A1 | 7/2021 | Chang et al. | |
| 2021/0201485 A1* | 7/2021 | Chukka | G06T 7/0012 |
| 2021/0397870 A1* | 12/2021 | Bredno | G01J 3/28 |
| 2022/0148176 A1* | 5/2022 | Bredno | G06T 7/62 |

FOREIGN PATENT DOCUMENTS

| | | |
|---|---|---|
| WO | WO 2003/105675 | 12/2003 |
| WO | WO 2013/177953 | 12/2013 |
| WO | WO 2018/231204 | 12/2018 |

OTHER PUBLICATIONS

Liu et al., "Microfluidic device as a new platform for immunofluorescent detection of viruses," Lab on a Chip, 2005, 5(11):1327-30.
International Search Report and Written Opinion in International Appln. No. PCT/US2020/065371, dated Apr. 9, 2021, 13 pages.

* cited by examiner

SYSTEM AND METHOD FOR ACQUISITION AND PROCESSING OF MULTIPLEXED FLUORESCENCE IN-SITU HYBRIDIZATION IMAGES

CROSS-REFERENCE TO RELATED APPLICATIONS

This application claims priority to U.S. Application Ser. No. 62/949,391, filed on Dec. 17, 2019, the disclosure of which is incorporated by reference.

TECHNICAL FIELD

This specification relates multiplexed fluorescence in-situ hybridization imaging.

BACKGROUND

It is of great interest to the biotech community and pharmaceutical industry to develop methods for visualizing and quantifying multiple biological analytes—e.g., DNA, RNA, and protein—within a biological sample—e.g., tissue resection, biopsy, cells grown in culture. Scientists use such methods to diagnose/monitor disease, validate biomarkers, and investigate treatment. To date, exemplary methods include multiplex imaging of antibodies or oligonucleotides (e.g., RNA or DNA) labeled with a functional domain to a biological sample.

Multiplexed fluorescence in-situ hybridization (mFISH) imaging is a powerful technique to determine gene expression in spatial transcriptomics. In brief, a sample is exposed to multiple oligonucleotide probes that target RNA of interest. These probes have different labeling schemes that will allow one to distinguish different RNA species when the complementary, fluorescent labeled probes are introduced to the sample. Then the sequential rounds of fluorescence images are acquired with exposure to excitation light of different wavelengths. For each given pixel, its fluorescence intensities from the different images for the different wavelengths of excitation light form a signal sequence. This sequence is then compared to a library of reference codes from a codebook that associates each code with a gene. The best matching reference code is used to identify an associated gene that is expressed at that pixel in the image.

SUMMARY

In one aspect, a fluorescent in-situ hybridization imaging system includes a flow cell to contain a sample to be exposed to fluorescent probes in a reagent, a valve to control flow from one of a plurality of reagent sources the flow cell, a pump to cause fluid flow through the flow cell, a fluorescence microscope including a variable frequency excitation light source and a camera positioned to receive fluorescently emitted light from the sample, an actuator to cause relative vertical motion between the flow cell and the fluorescence microscope, a motor to cause to cause relative lateral motion between the flow cell and the fluorescence microscope, and a control system. The control system is configured to, as nested loops, cause the valve to sequentially couple the flow cell to a plurality of different reagent sources to expose the sample to a plurality of different reagents, for each reagent of the plurality of different reagents, cause the motor to sequentially position the fluorescence microscope relative to sample at a plurality of different fields of view, for each field of view of the plurality of different fields of view, cause the variable frequency excitation light source to sequentially emit a plurality of different wavelengths, for each wavelength of the plurality of different wavelengths, cause the actuator to sequentially position the fluorescence microscope relative to sample at a plurality of different vertical heights, and for each vertical height of the plurality of different vertical heights, obtain an image at the respective vertical height covering the respective field of view of the sample having respective fluorescent probes of the respective regent as excited by the respective wavelength.

In another aspect, a fluorescent in-situ hybridization imaging and analysis system includes a flow cell to contain a sample to be exposed to fluorescent probes in a reagent, a fluorescence microscope to obtain sequentially collect a plurality of images of the sample at a plurality of different combinations of imaging parameters, and a data processing system. The data processing system includes an online pre-processing system configured to sequentially receive the images from the fluorescence microscope as the images are collected and perform on-the-fly image pre-processing to remove experimental artifacts of the image and to provide RNA image spot sharpening, and an offline processing system configured to, after the plurality of images are collected, perform registration of images having a same field of view and to decode intensity values in the plurality of images to identify expressed genes.

In another aspect, a fluorescent in-situ hybridization imaging system includes a flow cell to contain a sample to be exposed to fluorescent probes in a reagent, a fluorescence microscope, and a control system. The fluorescence microscope includes a variable frequency excitation light source to illuminate the sample, a plurality of emission bandpass filters on a filter wheel, an actuator to rotate the filter wheel, and a camera positioned to receive fluorescently emitted light from the sample that has passed through a filter on the filter wheel. The control system is configured to cause the variable frequency excitation light source to emit a light beam having a selected wavelength, cause the actuator to rotate the filter wheel to position a selected filter in a light path between the sample and the camera, obtain an image from the camera, and coordinate the variable frequency excitation light source and filter wheel such that the selected filter has an emission bandpass associated with emission by the fluorescent probes when excited by the selected wavelength when the image is obtained.

In another aspect, a computer program product has instructions to cause one or more processors to apply one or more filters to and perform deconvolution on each image of the plurality of images to generate a plurality of filtered images, perform registration of the plurality of filtered images to generate a plurality of registered and filtered images, for each pixel of at least two pixels of the plurality of registered and filtered images decode the pixel by identifying a code word from a plurality of code words in a code book that provides a best match to data values in the plurality of registered and filtered images for the pixel, and for each pixel of at least two pixels, determine a gene associated with the code word and store an indication that the gene is expressed at the pixel.

In another aspect, a computer program product has instructions to receive a plurality of initial images of a sample, the plurality of initial images sharing a common field of view. For each initial image of the plurality of initial images, the initial image is split into a plurality of sub-images of equal size, a combined image of size equal to that of a sub-image is calculated from the plurality of sub-images to thereby generate a plurality of reduced-size images with each image of the plurality of images having a corresponding reduced-size image, for at least one reduced-size images of the plurality of reduced-size images a transform is determined to register the plurality of reduced-size images, for each of the at least one reduced-size images the transform determined for the reduced-size image is applied to the corresponding initial image to generate a transformed image of size equal to the initial image and thereby generate a plurality of transformed images, and for each pixel of at least two pixels of the plurality of transformed images the pixel is decoded by identifying a code word from a plurality of code words in a code book that provides a best match to data values in the plurality of transformed images for the pixel. For each pixel of at least two pixels, a gene associated with the code word is determined and an indication that the gene is expressed at the pixel is stored.

In another aspect, a computer program product has instructions to receive a plurality of images representing a common field of view of a sample, perform registration of the plurality of images to generate a plurality of registered images, for each pixel of a plurality of pixels of the registered images decode the pixel by identifying a code word from a plurality of code words in a code book that provides a best match to data values in the plurality of registered images for the pixel, and for each code word identified as a best match for one or more pixels and each pixel of the one or more pixels determine whether a bit ratio for an image word for the pixel meets a threshold for the code word. The image word is formed from the data values in the plurality of registered images for the pixel. For at least one pixel that is determined to meet the threshold a gene associated with the code word is determined and an indication is stored that the gene is expressed at the pixel. Pixels for which the bit ratio does not meet the threshold are screened.

In another aspect, a computer program product has instructions to receive a plurality of images representing a common field of view of a sample, perform registration of the plurality of images to generate a plurality of registered images, for each pixel of a plurality of pixels of the registered images decode the pixel by identifying a code word from a plurality of code words in a code book that provides a best match to data values in the plurality of registered images for the pixel, and for each code word identified as a best match for one or more pixels and each pixel of the one or more pixels whether a bit brightness for an image word for the pixel meets a threshold for the code word is determined. The image word is formed from the data values in the plurality of registered images for the pixel. For each pixel that is determined to meet the threshold a gene associated with the code word is determined and an indication is stored that the gene is expressed at the pixel. Pixels for which the bit ratio does not meet the threshold are screened.

In another aspect, a computer program product has instructions to receive a plurality of initial images of a sample. The plurality of initial images including a multiplicity of images for each field of view of a plurality of different fields of view. Instructions are stored to perform an image processing algorithm in which one or more of image filtering of the multiplicity of images for the field of view or registration of the multiplicity of images for the field of view. For each field of view, one or more initial parameter values are determined, wherein different fields of view have different initial parameter values. The image processing algorithm is performed for each field of view using the different initial decoding parameter values for the different fields of view. One or more subsequent decoding parameter values are determined, and the image processing algorithm and a decoding algorithm are performed for each field of view using the same subsequent parameter values for the different fields of view to generate a set of spatial transcriptomic data.

In another aspect, a computer program product has instructions to receive a plurality of initial images of a sample, the plurality of initial images including a multiplicity of images for each field of view of a plurality of different fields of view. For each field of view, a set of spatial transcriptomic data is generated based on the multiplicity of images for the field of view. Each set of spatial transcriptomic data includes one or more data pairs, each data pair of the one or more data pairs including a position and an expressed gene for that position. Regions of overlap of multiplicities of images from adjacent fields of view are determined. From the set of spatial transcriptomic data for each field of view, a combined set of spatial transcriptomic data is generated for a combined image covering the plurality of different fields of view. In generating the combined set of spatial transcriptomic data, at least one double-counted data pair from different fields of view that represents the same expressed gene at the same location within the sample is screened.

In another aspect, a computer program product has instructions to receive a plurality of images of a sample, the plurality of images including a multiplicity of images for each field of view of a plurality of different fields of view. On each image of the plurality of images, an image quality check is performed on the image. After performing the image quality check, artifacts are removed from each image of the plurality of images. After removing artifacts, image spots are sharpened in each image of the plurality of images. After sharpening the image spots, for each multiplicity of images, registration of the multiplicity of images is performed to generate a plurality of registered images. After performing registration, for each multiplicity of images, and for each pixel of a plurality of pixels of the registered images of a respective multiplicity, the pixel is decoded by identifying a code word from a plurality of code words in a code book that provides a best match to data values in the respective multiplicity of registered images for the pixel.

Advantages of implementations can include, but are not limited to, one or more of the following.

The acquisition of multiplexed fluorescence in-situ hybridization (mFISH) images and subsequent processing to determine gene expression can be automated in a manner suitable for industrial adoption. Large sample sizes that require multiple fields-of-view (FOVs) can be processed with uniform image quality. Run-to-run consistency in multi-sample or multi-modal research can be improved. Fluorescence images of the same FOV captured at different times can be registered without using separate fiducials, e.g., without requiring fiducial beads, and using fewer computational resources and more accurately than some conventional techniques.

The details of one or more embodiments are set forth in the accompanying drawings and the description below. Other features, aspects, and advantages will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
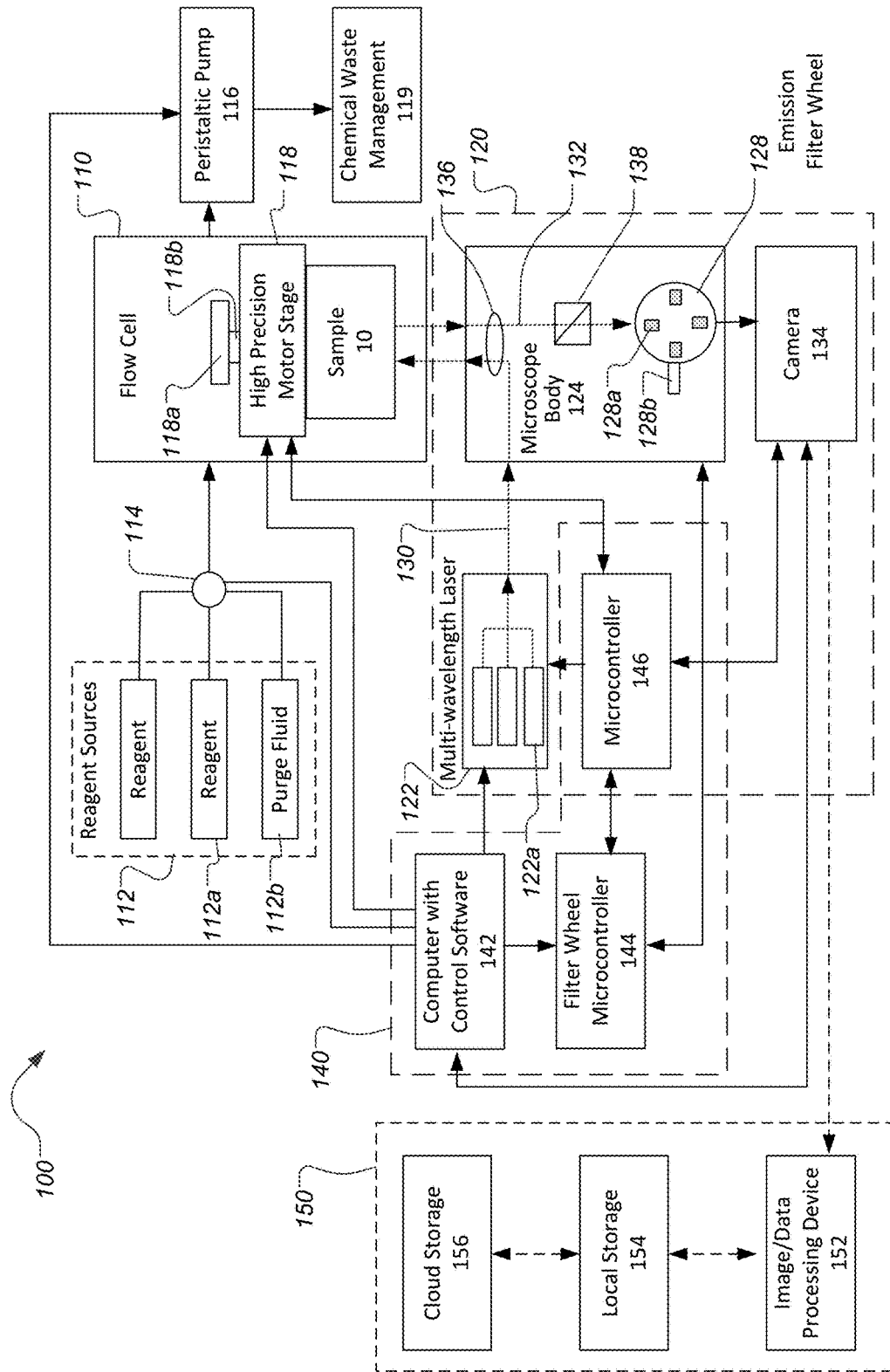
FIG. 1 is a schematic diagram of an apparatus for multiplexed fluorescence in-situ hybridization imaging.

Although multiplexed fluorescence in-situ hybridization (mFISH) imaging is a powerful technique, it has so far been used primarily in an academic context. Use of the technique for spatial transcriptomics in an industry context, e.g., by a biotechnology company performing research using mFISH for spatial transcriptomic to develop pharmaceuticals intended for productization, poses a variety of issues. For example:

The system should be fully or nearly fully automated so that a user, e.g., a research scientist who is familiar with biology but not with image processing or software programming techniques, need merely enter parameters relating to the biological aspects being investigated, and need not make decisions relating to image processing or have programming expertise. Such automation is not, in fact, trivial, and contains a variety of pitfalls.

The current state-of-art takes sample images from generic optical microscopes with small image sizes that are suitable for small samples. The samples utilized in the industrial context can be larger and may require multiple fields of view to completely image. Such multiple FOVs can be stitched manually, but semi-automatic approaches suffer from possible issues such as poor image registration, over-counting of expressed genes, or lack of reliability due to inconsistency in processing of different regions of the stitched image.

The process needs a sufficiently high throughput to be industrially feasible. However, current state-of-the-art takes considerable imaging time and requires many manual steps in data analysis. A higher imaging throughput and quality control is needed for large-scale life science and clinical research. Moreover, the scalability of data processing is limited by computation time.

Because each FOV is processed individually, significant variation across a region of interest can be found. In addition, images from different instruments need to be well-calibrated and converted before being sent to a software pipeline. Conventionally, the image processing parameters need to be adjusted manually to accommodate system or sample variation.

Current solutions have a strong assumption of perfect images, which creates a gap between experimental condition and the calibration method.

An overall architecture and a variety of individual components and steps are discussed below that can address one or more of the above issues.

In general, the overall architecture and individual components and steps enable an end-to-end mFISH imaging and decoding process that involves minimal manual steps. The system integrates fully automatic hardware architecture and on-the-fly image processing. The methods include feedback control, image calibration, and global optimization. The end-to-end process time can be reduced and throughput per sample can be increased. The apparatus can be easy to use by a research scientist in an industry context. Control metrics can ensure data quality before downstream analysis; the early detection reduces waste of samples. The algorithm can enable scalability to large imaging areas with uniform and consistent spatial gene expression. Data accuracy and repeatability for large-scale study can be improved; the results can be easily interpreted and further analyzed in software packages.

Referring to FIG. 1, a multiplexed fluorescent in-situ hybridization (mFISH) imaging and image processing apparatus 100 includes a flow cell 110 to hold a sample 10, a fluorescence microscope 120 to obtain images of the sample 10, and a control system 140 to control operation of the various components of the mFISH imaging and image processing apparatus 100. The control system 140 can include a computer 142, e.g., having a memory, processor, etc., that executes control software.

The fluorescence microscope 120 includes an excitation light source 122 that can generate excitation light 130 of multiple different wavelengths. In particular, the excitation light source 122 can generate narrow-bandwidth light beams having different wavelengths at different times. For example, the excitation light source 122 can be provided by a multi-wavelength continuous wave laser system, e.g., multiple laser modules 122a that can be independently activated to generate laser beams of different wavelengths. Output from the laser modules 122a can be multiplexed into a common light beam path.

The fluorescence microscope 120 includes a microscope body 124 that includes the various optical components to direct the excitation light from the light source 122 to the flow cell 110. For example, excitation light from the light source 122 can be coupled into a multimode fiber, refocused and expanded by a set of lenses, then directed into the sample by a core imaging component, such as a high numerical aperture (NA) objective lens 136. When the excitation channel needs to be switched, one of the multiple laser modules 122a can be deactivated and another laser module 122a can be activated, with synchronization among the devices accomplished by one or more microcontrollers 144, 146.

The objective lens 136, or the entire microscope body 124, can be installed on vertically movable mount coupled to a Z-drive actuator. Adjustment of the Z-position, e.g., by a microcontroller 146 controlling the Z-drive actuator, can enable fine tuning of focal position. Alternatively, or in addition, the flow cell 110 (or a stage 118 supporting the sample in the flow cell 110) could be vertically movable by a Z-drive actuator 118b, e.g., an axial piezo stage. Such a piezo stage can permit precise and swift multi-plane image acquisition.

The sample 10 to be imaged is positioned in the flow cell 110. The flow cell 110 can be a chamber with cross-sectional area (parallel to the object or image plane of the microscope) with and area of about 2 cm by 2 cm. The sample 10 can be supported on a stage 118 within the flow cell, and the stage (or the entire flow cell) can be laterally movable, e.g., by a pair of linear actuators 118a to permit XY motion. This permits acquisition of images of the sample 10 in different laterally offset fields of view (FOVs). Alternatively, the microscope body 124 could be carried on a laterally movable stage.

An entrance to the flow cell 110 is connected to a set of hybridization reagents sources 112. A multi-valve positioner 114 can be controlled by the controller 140 to switch between sources to select which reagent 112a is supplied to the flow cell 110. Each reagent includes a different set of one or more oligonucleotide probes. Each probe targets a different RNA sequence of interest, and has a different set of one or more fluorescent materials, e.g., phosphors, that are excited by different combinations of wavelengths. In addition to the reagents 112a, there can be a source of a purge fluid 112b, e.g., DI water.

An exit to the flow cell 110 is connected to a pump 116, e.g., a peristaltic pump, which is also controlled by the controller 140 to control flow of liquid, e.g., the reagent or purge fluid, through the flow cell 110. Used solution from the flow cell 110 can be passed by the pump 116 to a chemical waste management subsystem 119.

In operation, the controller 140 causes the light source 122 to emit the excitation light 130, which causes fluorescence of fluorescent material in the sample 10, e.g., fluorescence of the probes that are bound to RNA in the sample and that are excited by the wavelength of the excitation light. The emitted fluorescent light 132, as well as back propagating excitation light, e.g., excitation light scattered from the sample, stage, etc., is collected by an objective lens 136 of the microscope body 124.

The collected light can be filtered by a multi-band dichroic mirror 138 in the microscope body 124 to separate the emitted fluorescent light from the back propagating illumination light, and the emitted fluorescent light is passed to a camera 134. The multi-band dichroic mirror 138 can include a pass band for each emission wavelength expected from the probes under the variety of excitation wavelengths. Use of a single multi-band dichroic mirror (as compared to multiple dichroic mirrors or a movable dichroic mirror) can provide improved system stability.

The camera 134 can be a high resolution (e.g., 2048×2048 pixel) CMOS (e.g., a scientific CMOS) camera, and can be installed at the immediate image plane of the objective. Other camera types, e.g., CCD, may be possible. When triggered by a signal, e.g., from a microcontroller, image data from the camera can be captured, e.g., sent to an image processing system 150. Thus, the camera 134 can collect a sequence of images from the sample.

To further remove residual excitation light and minimize cross talk between excitation channels, each laser emission wavelength can be paired with a corresponding band-pass emission filter 128a. Each filter 128a can have a wavelength of 10-50 nm, e.g., 14-32 nm. In some implementations, a filter is narrower than the bandwidth of the fluorescent material of the probe resulting from the excitation, e.g., if the fluorescent material of the probe has a long trailing spectral profile.

The filters are installed on a high-speed filter wheel 128 that is rotatable by an actuator 127b. The filter wheel 128 can be installed at the infinity space to minimize optical aberration in the imaging path. After passing the emission filter of the filter wheel 128, the cleaned fluorescence signals can be refocused by a tube lens and captured by the camera 134. The dichroic mirror 138 can be positioned in the light path between the objective lens 138 and the filter wheel 128.

To facilitate high speed, synchronized operation of the system, the control system 140 can include two microcontrollers 144, 146 that are employed to send trigger signals, e.g., TTL signals, to the components of the fluorescence microscope 120 in a coordinated manner. The first microcontroller 144 is directly run by the computer 142, and triggers actuator 128b of the filter wheel 128 to switch emission filters 128a at different color channels. The first microcontroller 144 also triggers the second microcontroller 146, which sends digital signals to the light source 122 in order to control which wavelength of light is passed to the sample 10. For example, the second microcontroller 146 can send on/off signals to the individual laser modules of the light source 122 to control which laser module is active, and thus control which wavelength of light is used for the excitation light. After completion of switching to a new excitation channel, the second microcontroller 146 controls the motor for the piezo stage 116 to select the imaging height. Finally the second microcontroller 146 sends a trigger signal to the camera 134 for image acquisition.

Communication between the computer 142 and the device components of the apparatus 100 is coordinated by the control software. This control software can integrate drivers of all the device components into a single framework, and thus can allow a user to operate the imaging system as a single instrument (instead of having to separately control many devices).

The control software supports interactive operations of the microscope and instant visualization of imaging results. In addition, the control software can provide a programming interface which allows users to design and automate their imaging workflow. A set of default workflow scripts can be designated in the scripting language.

In some implementations, the control system 140 is configured, i.e., by the control software and/or the workflow script, to acquire fluorescence images (also termed simply "collected images" or simply "images") in loops in the following order (from innermost loop to outermost loop): z-axis, color channel, lateral position, and reagent.

These loops may be represented by the following pseudo-code:

```
for h=1:N_hybridization
   % multiple hybridizations
   for f=1:N_FOVs
      % multiple lateral field-of-views
      for c=1:N_channels
         % multiple color channels
         for z=1:N_planes
            % multiple z planes
            Acquire image(h, f, c, z);
         end % end for z
      end % end for c
   end % end for f
end % end for h
```

For the z-axis loop, the control system 140 causes the stage 118 to step through multiple vertical positions. Because the vertical position of the stage 118 is controlled by a piezoelectric actuator, the time required to adjust positions is small and each step in this loop is extremely fast.

First, the sample can be sufficiently thick, e.g., a few microns, that multiple image planes through the sample may be desirable. For example, multiple layers of cells can be present, or even within a cell there may be a vertical variation in gene expression. Moreover, for thin samples, the vertical position of the focal plane may not be known in advance, e.g., due to thermal drift. In addition, the sample 10 may vertically drift within the flow cell 110. Imaging at multiple Z-axis positions can ensure most of the cells in a thick sample are covered, and can help identify the best focal position in a thin sample.

For the color channel loop, the control system 140 causes the light source 122 to step through different wavelengths of excitation light. For example, one of the laser modules is activated, the other laser modules are deactivated, and the emission filter wheel 128 is rotated to bring the appropriate filter into the optical path of the light between the sample 10 and the camera 134.

For the lateral position, the control system 140 causes the light source 122 to step through different lateral positions in order to obtain different fields of view (FOVs) of the sample. For example, at each step of the loop, the linear actuators supporting the stage 118 can be driven to shift the stage laterally. In some implementations, the control system 140 number of steps and lateral motion is selected such that the accumulated FOVs to cover the entire sample 10. In some implementations, the lateral motion is selected such that FOVs partially overlap.

For the reagent, the control system 140 causes the apparatus 100 to step through multiple different available reagents. For example, at each step of the loop, the control system 140 can control the valve 114 to connect the flow cell 110 to the purge fluid 112b, cause the pump 116 to draw the purge fluid through the cell for a first period of time to purge the current reagent, then control the valve 114 to connect the flow cell 110 to different new reagent, and then draw the new reagent through the cell for a second period of time sufficient for the probes in the new reagent to bind to the appropriate RNA sequences. Because some time is required to purge the flow cell and for the probes in the new reagent to bind, the time required to adjust reagents in is the longest, as compared to adjusting the lateral position, color channel or z-axis.

As a result, a fluorescence image is acquired for each combination of possible values for the z-axis, color channel (excitation wavelength), lateral FOV, and reagent. Because the innermost loop has the fastest adjustment time, and the successively surrounding loops are of successively slower adjustment time, this configuration provides the most time efficient technique to acquire the images for the combination of values for these parameters.

A data processing system 150 is used to process the images and determine gene expression to generate the spatial transcriptomic data. At a minimum, the data processing system 150 includes a data processing device 152, e.g., one or more processors controlled by software stored on a computer readable medium, and a local storage device 154, e.g., non-volatile computer readable media, that receives the images acquired by the camera 134. For example, the data processing device 152 can be a work station with GPU processors or FPGA boards installed. The data processing system 150 can also be connected through a network to remote storage 156, e.g., through the Internet to cloud storage.

In some implementations, the data processing system 150 performs on-the-fly image processing as the images are received. In particular, while data acquisition is in progress, the data processing device 152 can perform image pre-processing steps, such as filtering and deconvolution, that can be performed on the image data in the storage device 154 but which do not require the entire data set. Because filtering and deconvolution are a major bottleneck in the data processing pipeline, pre-processing as image acquisition is occurring can significantly shorten the offline processing time and thus improve the throughput.

Figure 2:
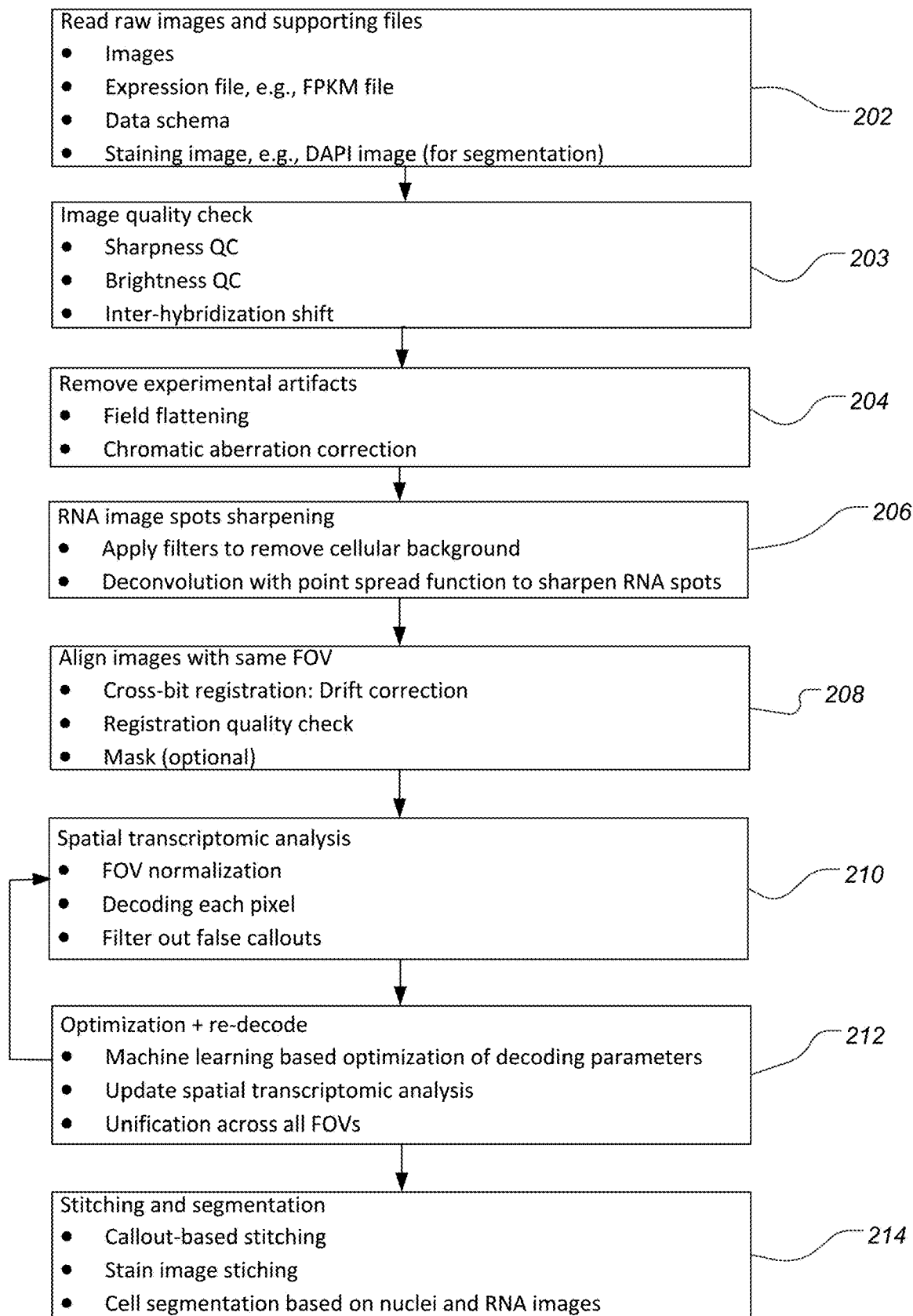
FIG. 2 is a flow chart of a method of data processing.

FIG. 2 illustrates a flow chart of a method of data processing in which the processing is performed after all of the images have been acquired. The process begins with the system receiving the raw image files and supporting files (step 202). In particular, the data processing system can receive the full set of raw images from the camera, e.g., an image for each combination of possible values for the z-axis, color channel (excitation wavelength), lateral FOV, and reagent.

In addition, the data processing system can receive a reference expression file, e.g., a FPKM (fragments per kilobase of sequence per million mapped reads) file, a data schema, and one or more stain images, e.g., DAPI images. The reference expression file can be used to cross-check between traditional sequence results and the mFISH results.

The image files received from the camera can optionally include metadata, the hardware parameter values (such as stage positions, pixel sizes, excitation channels, etc.) at which the image was taken. The data schema provides a rule for ordering the images based on the hardware parameters so that the images are placed into one or more image stacks in the appropriate order. If metadata is not included, the data schema can associate an order of the images with the values for the z-axis, color channel, lateral FOV and reagent used to generate that image.

The stain images will be presented to the user with the transcriptomic information overlaid.

The collected images can be subjected to one or more quality metrics (step 203) before more intensive processing in order to screen out images of insufficient quality. Only images that meet the quality metric(s) are passed on for further processing. This can significantly reduce processing load on the data processing system In order to detect focusing failures, a sharpness quality value can be determined for each collected image. As an example, sharpness quality can be calculated by summing the gradient in intensity over the image:

$$S=\int dx dy \sqrt{|\nabla I(x,y)|^2}$$

If the sharpness quality value is below a threshold, then that image can be identified as out of focus. The threshold can be a preset empirically determined value, or the threshold can be calculated based on the sharpness values for the images with the same FOV. For example, a standard deviation of sharpness quality values can be calculated, the threshold can be set based on the standard deviation.

As noted above, the z-axis position of the focal plane might not be known exactly. Images are out of focus can be screened out. In some implementations, in each z-axis loop, only a single image is retained, e.g., the image having the best sharpness quality. In some implementation, multiple images from a single each z-axis loop can meet the sharpness quality, and the multiple images are combined, e.g., blended, to form a single image.

In order to detect regions of interest, a brightness quality value can be determined for each collected image. The brightness quality can be used to determine whether any cells are present in the image. For example, the intensity values of all the pixels in the image can be summed and compared to a threshold. If the total is less than the threshold, then this can indicate that there is essentially nothing in the image, i.e., no cells are in the image, and there is no information of interest and the image need not be processed. As another example, a standard deviation of the intensity values in the image can be calculated and compared to a threshold. If the standard deviation is below the threshold, this indicates that the image is fairly uniform and may lack bright spots indicating excited probes. Again, such a collected image does not have information of interest and the image need not be processed.

The above two quality checks are exemplary and other quality metrics can be used. Fore example, quality metric that measures spot quality can be used.

Another quality check can detect inter-hybridization shift. If there is significant sample drift occurring between rounds of imaging, then the subsequent registration may be unreliable. Sample drift can be detected by a variety of image processing algorithms, e.g., phase-correlation. In particular, a collected image can be compared to an image for the same FOV but for a prior reagent. If the images are not sufficiently correlated, e.g., does not meet a threshold correlation, the collected image does not have information of interest and the image need not be processed.

Next, each image is processed to remove experimental artifacts (step 204). Since each RNA molecule will be hybridized multiple times with probes at different excitation channels, a strict alignment across the multi-channel, multi-round image stack is beneficial for revealing RNA identities over the whole FOV. Removing the experimental artifacts can include field flattening and/or chromatic aberration correction In some implementations, the field flattening is performed before the chromatic aberration correction.

Imperfections of the illumination profile (e.g., Gaussian or other uneven distributions instead of uniform distribution across the FOV) in the excitation light can lead to uneven fluorescent signal level across the FOV, and this spatial unevenness often varies between excitation channels. Such nonuniformity can be passed to from illumination field to fluorescent signal level across the FOV, and consequently bias the spatial transcriptomic analysis results. To eliminate this artifact, an illumination profile, e.g., test image, is measured for each color channel using a fluorescent target with uniform fluorophore density within the FOV. These measured illumination profiles are then used as channel-specific normalization factors in imaging data. For example, the illumination profile for each color channel (i.e., each emission wavelength to be measured) can be stored as a normalization image, and the intensity value for each pixel in a collected image for a color channel is divided by the intensity value for the corresponding pixel in the normalization image of the associated color channel.

Chromatic aberration correction accounts for optical distortions that vary across the different emission channels. That is, because the probes are being measured for different wavelengths, chromatic aberrations in the imaging path, if any, may significantly degrade the downstream analysis results. To maintain the robustness of analysis results against this potential hardware defect, a software-based solution for chromatic aberration correction can be provided in the data processing pipeline. In particular, a test image is generated for each color channel using a target having fluorescent spots in a known pattern, e.g., a rectangular pattern. For each color channel, a transform is calculated that brings the measured spots in the test image back into alignment with the known pattern. These transforms are stored, and in normal operation when images of a sample are being collected, an appropriate transform is selected and applied to each collected image based on the color channel for that collected image.

Each image is processed to provide RNA image spot sharpening (step 206). RNA image spot sharpening can include applying filters to remove cellular background and/or deconvolution with point spread function to sharpen RNA spots.

In order to distinguish RNA spots from relatively bright background, a low-pass filter is applied to the image, e.g., to the field-flattened and chromatically corrected images to remove cellular background around RNA spots. The filtered images are further de-convolved with a 2-D point spread function (PSF) to sharpen the RNA spots, and convolved with a 2-D Gaussian kernel with half pixel width to slightly smooth the spots.

The images having the same FOV are registered to align the features, e.g., the cells or cell organelles, therein (step 208). To accurately identify RNA species in the image sequences, features in different rounds of images are aligned, e.g., to sub-pixel precision. However, since an mFISH sample is imaged in aqueous phase and moved around by a motorized stage, sample drifts and stage drifts through hours-long imaging process can transform into image feature shifts, which can undermine the transcriptomic analysis if left unaddressed. In other words, even assuming precise repeatable alignment of the fluorescence microscope to the flow cell or support, the sample may no longer be in the same location in the later image, which can introduce errors into decoding or simply make decoding impossible.

One conventional technique to register images is to place fiducial markers, e.g., fluorescent beads, within the carrier material on the slide. In general, the sample and the fiducial marker beads will move approximately in unison. These beads can be identified in the image based on their size and shape. Comparison of the positions of the beads permits registration of the two images, e.g., calculation of an affine transformation.

However, it may be possible to register images without the use of fluorescent beads or similar fiducial markers, but simply using the data within the image. In particular, high intensity regions should generally be located at the same position across multiple images of the same.

FOV. Techniques that can be used for registration between images include phase-correlation algorithms and mutual-information (MI) algorithms. The MI algorithm is generally more precise and robust than the phase-correlation algorithms. Therefore, a mutual-information (MI) based drift correction method can be used for alignment. However, the precision can come at an expense of high computational time.

Figure 3:
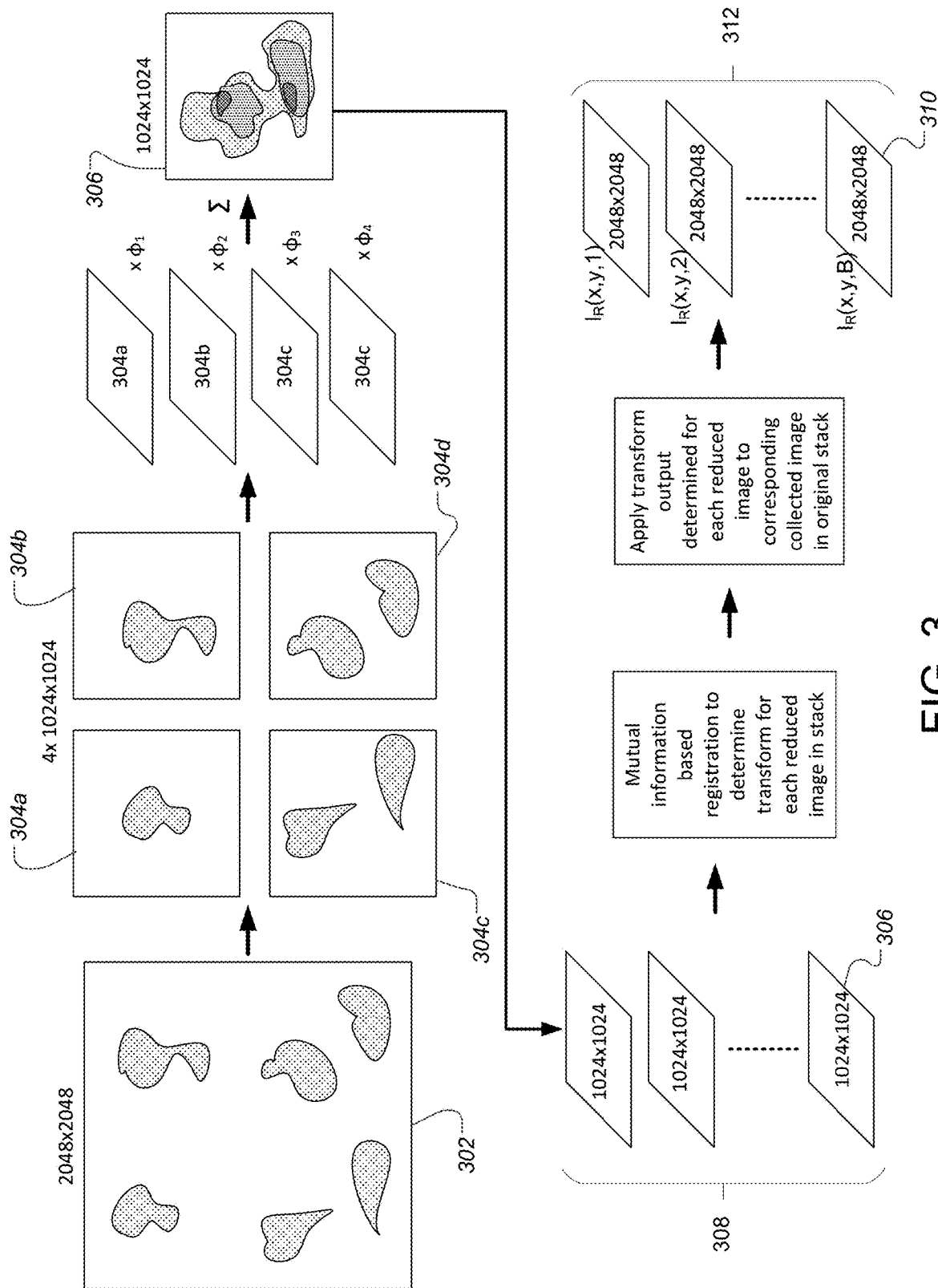
FIG. 3 schematically illustrates an image registration process that uses a mutual-information algorithm.

FIG. 3 illustrates a process for using a mutual-information algorithm to align collected images having the same FOV that preserves high precision of the MI registration algorithm while reducing computational load. The set of collected images having the same FOV can be considered an original image stack; the order of images in the stack is set by the data schema discussed above. Each collected image 302 in the image stack may be, for example, 2048×2048 pixels. In general, performing a mutual-information algorithm on an image of this size may require excessive computational power. The collected image 302 is evenly sliced into four image patches 304a, 304b, 304c, 304d. Assuming each collected image 302 is 2048×2048 pixels, then the image patches are 1024×1024 pixels. Each image patch 304a, 304b, 304c, 304d is multiplied by a phase factor 0.1), the phase shifted image patches are overlapped and summed to generate a complex image, and the real and imaginary parts of the complex image are summed up to create a summed image 306. This summed image 306 has ¼ size of the original image 302, e.g., is 1024×1024 pixels.

This process is repeated for each original image 302 in the original image stack to generate a stack 308 of images 306 of reduced side. The mutual-information algorithm is then performed using the stack 308 to generate a transform for each reduced image 306 in the stack 306. The transform can include a translation and/or scaling transform. To align the images in the original stack, the transform determined for each reduced image is applied to the corresponding collected image in the original stack. This should result in a stack 312 of collected images 310 of the original size, e.g., 2048×2048 pixels, in which the images 310 for the same FOV are in alignment.

This slice-and-overlap strategy preserves most of the features in the image and thus should still have high precision, but reduces the temporary image size for shift calculation and thus has reduced computational load. Although FIG. 3 and the discussion above focuses on splitting into four patches corresponding to upper right, lower right, upper left and lower left quadrants of the original image, another number of patches can be used, e.g., the image can be split into other shapes, e.g., rectangular rather than square, so long as the patches have the same dimensions. For example, the original image could be split into 8 image patches of 256×2048 pixels. In general, the image can be split into a rectangular grid having a plurality of columns and a plurality of rows, e.g., an equal number of columns and rows. The image can be split into N images, where $N=Z^2$ and Z is an even number integer (N=2 for the example in FIG. 3).

Returning to FIG. 2, because the filtering and deconvolution processes of step 206 are implemented on individual frames (i.e., bits) independently, they can be conducted prior to the registration of step 208. Moreover, since image stacks used for registration are background corrected and sharpened to reveal spatial features of RNA spots, the registration precision can be improved. To validate the latter advantage, three data sets from low confluency cell sample, high confluency cell sample, and brain tissue sample were compared for registration precision with registration first vs. filter first approaches. The registration quality was evaluated by summing up the registered image stack across all the layers, then calculating the maximum and the minimum of the summed image. The filter-first approach generally yields a larger maximum and smaller minimum of the flattened image, which indicates an improvement of the registration quality.

A registration quality check can be performed after registration. If properly registered, the bright points in each image should overlap so that the total brightness is increased. Referring the stack of unregistered images can be summed, and similarly the stack 312 of registered images 310 (see FIG. 3) can be summed, e.g.:

$$I_U(x, y) = \sum_{i=1}^{B} I_U(x, y, i)$$

$$I_R(x, y) = \sum_{i=1}^{B} I_R(x, y, i)$$

The maximum value of $I_U(x,y)$ can be compared to the maximum value of $I_R(x,y)$. If $\max(I_R(x,y)) > \max(I_U(x,y))$ then registration can be considered a success. On the other hand, if $\max(I_R(x,y)) \leq \max(I_U(x,y))$, the data processing system can indicate the registration is a failure and issue an error code. This FOV might be excluded from subsequent analysis and/or new images may need to be obtained.

Optionally, after registration, a mask can be calculated for each collected image. In brief, the intensity value for each pixel is compared to a threshold value. A corresponding pixel in the mask is set to 1 if the intensity value is above the threshold, and set to 0 if the intensity value is below the threshold. The threshold value can be an empirically determined predetermined value, or can be calculated from the intensity values in the image. In general, the mask can correspond to the location of cells within the sample; spaces between cells should not fluoresce and should have a low intensity.

To create masks, for each field of view, a compressed frame P(x,y) is created from the image sequence for that FOV. The compressed frame $\mathcal{P}(x,y)$ can be generated by performing a product operation on the images for that FOV, e.g.:

$$\mathcal{P}(x, y) = \prod_{i}^{B} I(x, y, i),$$

where i represents a layer number in the stack 312 of registered images 310 (see FIG. 3). A threshold can be generated based on the histogram of log $\mathcal{P}(x,y)$.

Figure 4:
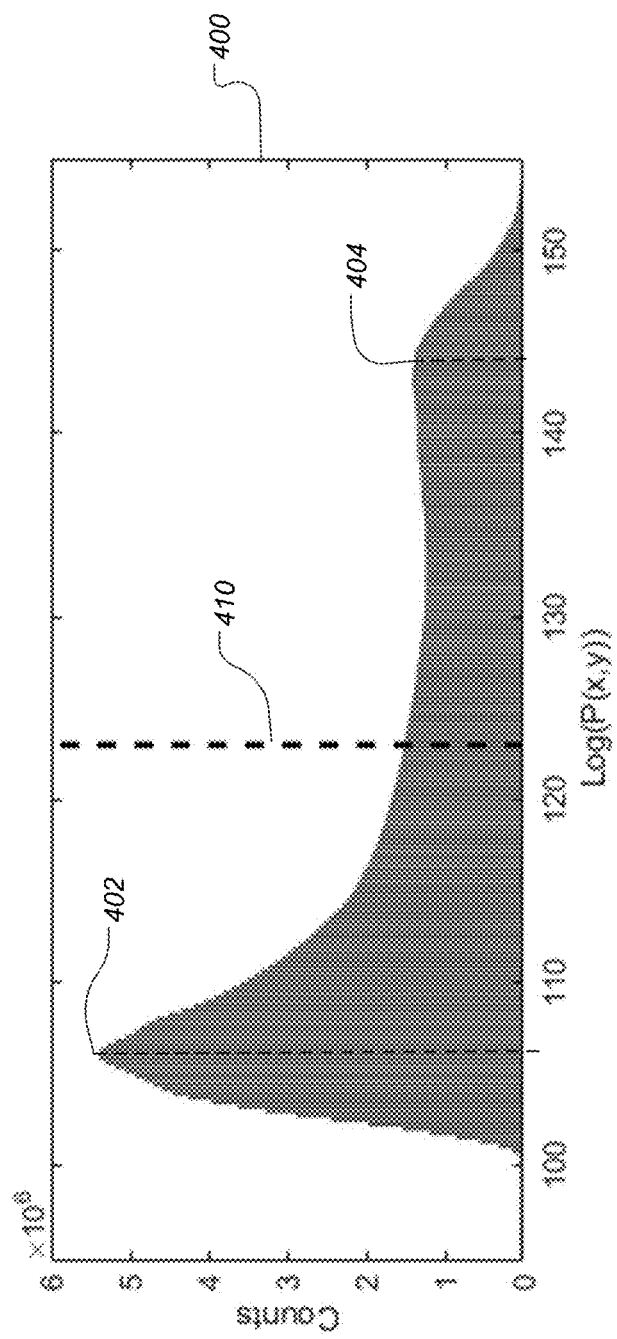
FIG. 4 is a logarithmic histogram of intensities in an image.

For example, FIG. 4 illustrates a logarithmic histogram 400 of compressed frame values ($\mathcal{P}(x,y)$) in a collected image. In general, the logarithmic histogram will include an initial sharp increase in intensity (which may be the leading edge of a first local maxima), and a final sharp decrease in intensity (which may be the trailing edge of a second local maxima). The histogram can be subjected to a peak and/or edge-finding algorithm to identify a first peak 402 that is closest to the lower end of the histogram (or an edge of the sharp increase in intensity if there is no clear peak) and a second peak 404 that is closest to the upper end of the histogram (or an edge of the sharp decrease in intensity if there is no clear peak). A threshold 410 can be set based on the intensity values of the two identified points 402, 404. For example, the threshold 410 can be an average of the intensity values. Instead of peak-finding, the histogram can be subjected to an Otsu threshold method to determine the threshold 410. A. This technique can be useful because the histogram does not always exhibit two clear peaks.

Salt and pepper effects can be removed from the mask. Single "on" pixels which are outside a continuous region of "on" pixels, or single "off" pixels which are inside a continuous region of "on" pixels can be converted to "off" or "on" to match the surrounding area. In general, clusters of adjacent pixels in the mask below a threshold size, e.g., 50 pixels, can be indicated as an error and be changed to match the surrounding area. By using masks, memory space can be conserved and computational workload can be reduced.

Figure 5B:
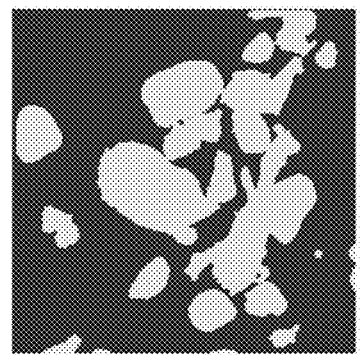
FIG. 5B is illustrates a mask generated from the image of FIG. 5A.
Figure 5A:
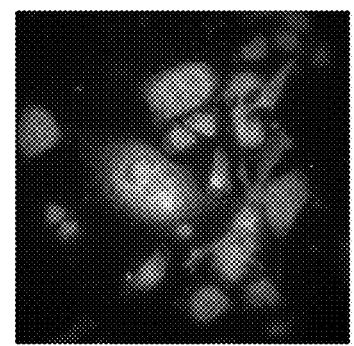
FIG. 5A is a collected image.

A collected image is illustrated in FIG. 5A, and FIG. 5B illustrates a mask resulting from the image of FIG. 5A.

Returning to FIG. 2, after registration of the images in a FOV, spatial transcriptomic analysis can be performed (step 210).

Figure 6A:
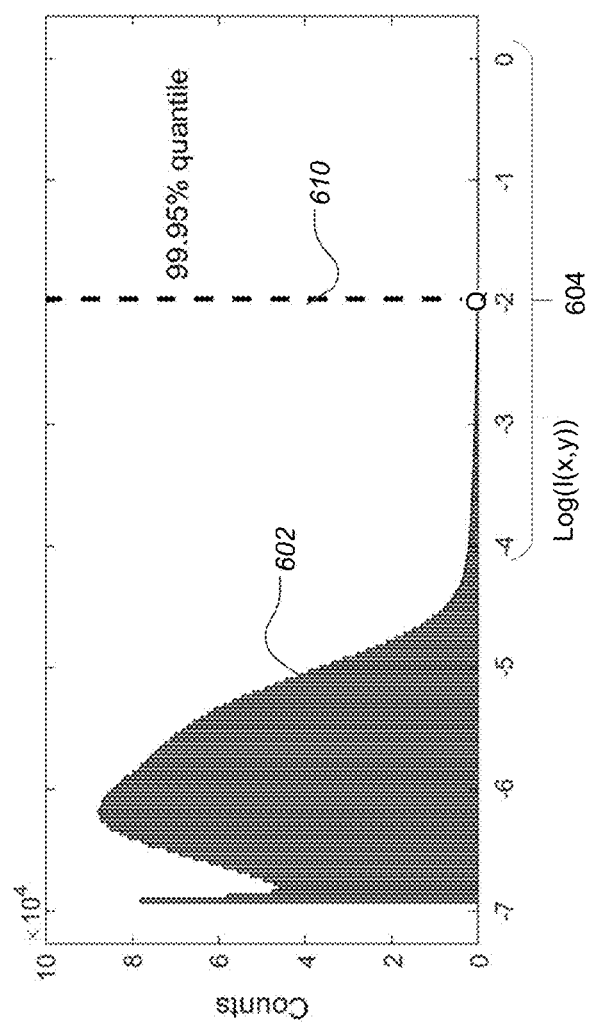
FIG. 6A is a logarithmic histogram of intensities from a filtered and de-convoluted image.

FOV normalization can be performed before the spatial transcriptomic analysis in order to make the histogram more consistent. In some implementations, the FOV normalization occurs after registration. Alternatively, FOV normalization can occur before registration. FOV normalization could be considered part of the filtering. A problem in the collected image, even after filtering and deconvolution discussed above, is that there can be a significant variation in brightness in the brightest pixels, e.g., over several orders of magnitude. For example, referring to FIG. 6A, the histogram 602 of intensity values in a collected image has a very long tail 604. This can introduce uncertainty in the decoding process. FOV normalization can counteract this source of error.

First, all the intensity values in the image are normalized relative to the maximum intensity value in the image. For example, the maximum intensity value is determined, and all intensity values are divided by the maximum so that intensity values vary between 0 and $I_{MAX}$, e.g., 1.

Figure 6B:
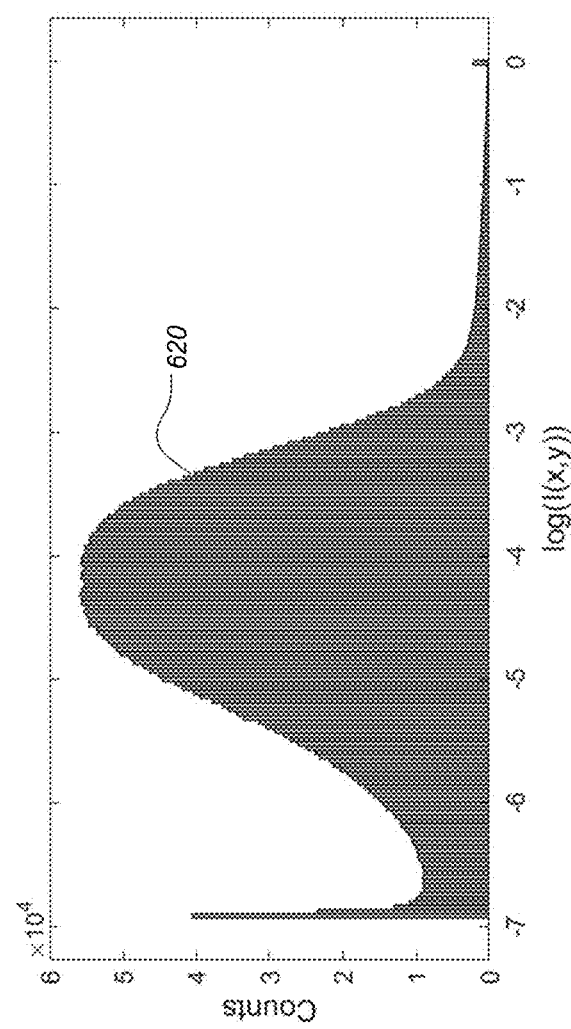
FIG. 6B is a logarithmic histogram of intensities after normalization.

Next the intensity values in the image are analyzed to determine an upper quantile that includes the highest intensity values, e.g., the 99% and higher quantile (i.e., upper 1%), 99.5% and higher quantile, or 99.9% and higher quantile, or 99.95% and higher quantile (i.e., upper 0.05%). The cutoff for this quantile is indicated by a broken line 610 in FIG. 6A. The intensity value at this quantile limit, e.g., the intensity value of log(−2) at the 99.95% quantile in the example of FIG. 6A, can be determined and stored. All pixels having intensity values within the upper quantile are reset to have the maximum intensity value, e.g., 1. Then the intensity values of the remaining pixels are scaled to run to the same maximum. To accomplish this, intensity values for the pixels that were not in the upper quantile are divided by the stored intensity value for the quantile limit. FIG. 6B illustrates the histogram 620 of intensity values resulting from the FOV normalization.

Decoding is explained with reference to FIG. 7. However, returning momentarily to FIG. 3, the aligned images for a particular FOV can be considered as a stack 312 that includes multiple image layers 310, with each image layer being X by Y pixels, e.g., 2048×2048 pixels. The number of image layers, B, depends on the combination of the number of color channels (e.g., number of excitation wavelengths) and number of hybridizations (e.g., number of reactants), e.g., B=N_hybridization*N_channels.

Figure 7:
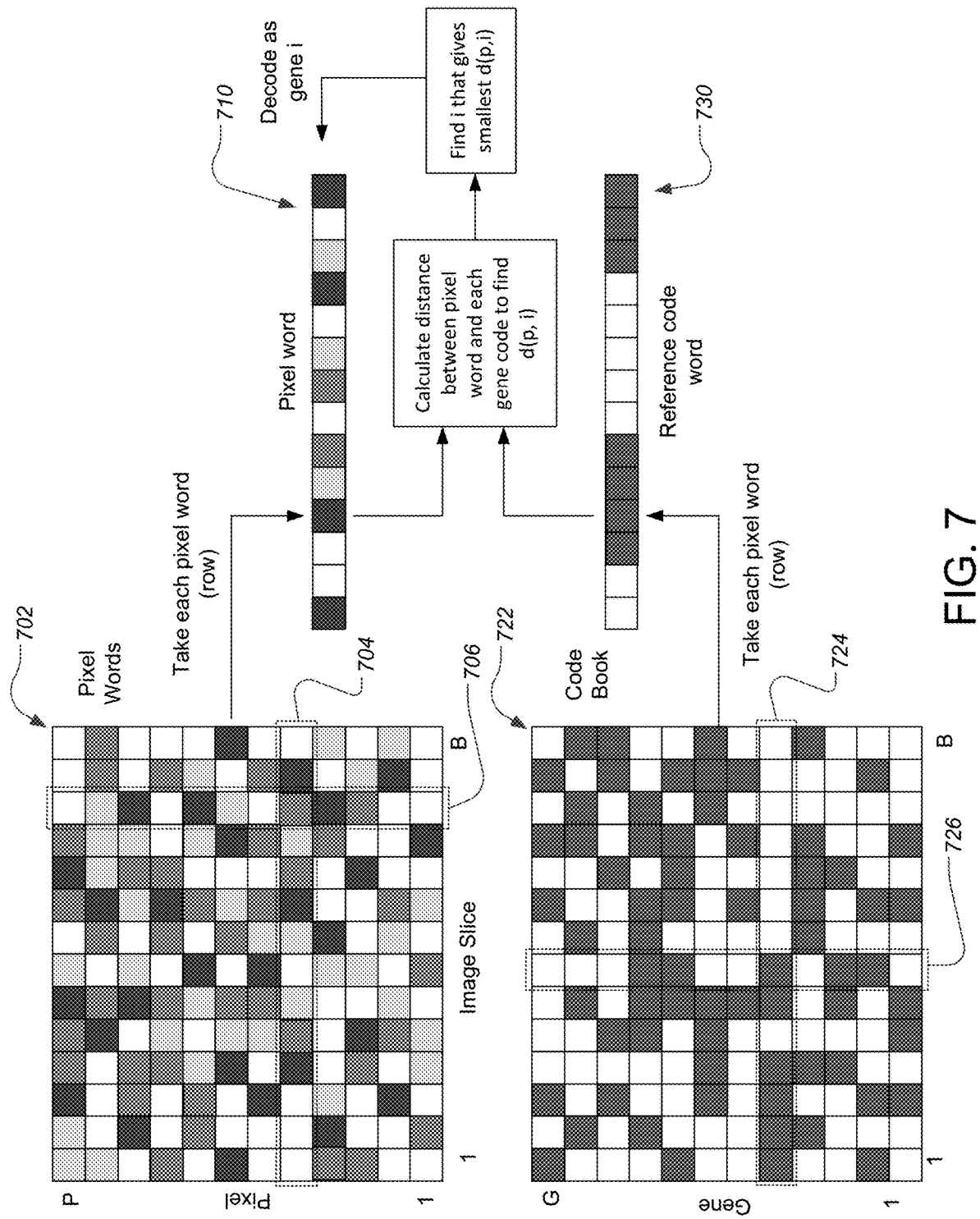
FIG. 7 illustrates a method of decoding.

Turning to FIG. 7, after normalization, this image stack can be evaluated as a 2-D matrix 702 of pixel words. The matrix 702 can have P rows 704, where P=X*Y, and B columns 706, where B is the number of images in the stack for a given FOV, e.g., N_hybridization*N_channels. Each row 704 corresponds to one of the pixels (the same pixel across the multiple image in the stack), the values from the row 704 provide a pixel word 710. Each column 706 provides one of the values in the word 710, i.e., the intensity value from the image layer for that pixel. As noted above, the values can be normalized, e.g., vary between 0 and $I_{MAX}$. Different intensity values are represented in FIG. 7 as different degrees of shading of the respective cells.

If all the pixels are passed to the decoding step, then all P words will be processed as described below. However, pixels outside cell boundaries can be screened out by the 2-D masks (see FIG. 4B above) and not processed. As result, computational load can be significantly reduced in the following analysis.

The data processing system 150 stores a code book 722 that is used to decode the image data to identify the gene expressed at the particular pixel. The code book 722 includes multiple reference code words, each reference code word associated with a particular gene. As shown in FIG. 7, the code book 722 can be represented as a 2D matrix with G rows 724, where G is the number of code words, e.g., the number of genes (although the same gene could be represented by multiple code words), and B columns 726. Each row 724 corresponds to one of the reference code words 730, and each column 706 provides one of the values in the reference code word 730, as established by prior calibration and testing of known genes. For each column, the values in the reference code 730 can be binary, i.e., "on" or "off". For example, each value can be either 0 or $I_{MAX}$, e.g., 1. The on and off values are represented in FIG. 7 by light and dark shading of respective cells.

For each pixel to be decoded, a distance d(p,i) is calculated between the pixel word 710 and each reference code word 730. For example, the distance between the pixel word 710 and reference code word 730 can be calculated as a Euclidean distance, e.g., a sum of squared differences between each value in the pixel word and the corresponding value in the reference code word. This calculation can be expressed as:

$$d(p, i) = \sum_{x=1}^{B}(I_{p,x} - C_{i,x})^2$$

where $I_{p,x}$ are the values from the matrix 702 of pixel words and $C_{i,x}$ are the values from the matrix 722 of reference code words. Other metrics, e.g., sum of absolute value of differences, cosine angle, correlation, etc., can be used instead of a Euclidean distance.

Once the distance values for each code word are calculated for a given pixel, the smallest distance value is determined, the code word that provides that smallest distance value is selected as the best matching code word. Stated differently, the data processing apparatus determines min (d(p,1), d(p,2), . . . d(p,B)), and determines the value b as the value for i (between 1 and B) that provided the minimum. The gene corresponding to that best matching code word is determined, e.g., from a lookup table that associates code words with genes, and the pixel is tagged as expressing the gene.

Returning to FIG. 2, the data processing apparatus can filter out false callouts. One technique to filter out false callouts is to discard tags where the distance value d(p,b) that indicated expression of a gene is greater than a threshold value, e.g., if d(p,b)>$D1_{MAX}$.

Yet another technique for filtering false callouts is to reject code words where a calculated bit ratio falls below a threshold. The bit ratio is calculated as the mean of the intensity values from the image word for layers that are supposed to be on (as determined from the code word), divided by the mean of the intensity values from the image word for layers that are supposed to be off (again as determined from the code word). For example, for the code word 730 shown in FIG. 7, the bits corresponding to columns 3-6 and 12-14 are on, and the bits corresponding to columns 1-2 and 7-11 are off. Thus, assuming this code word is selected as the best match for a pixel p, the bit ratio BR can be calculated as $$BR = \frac{[I(p, 3) + I(p, 4) + I(p, 5) + I(p, 6) + I(p, 12) + I(p, 13) + I(p, 14)]/7}{[I(p, 1) + I(p, 2) + I(P, 7) + I(p, 8) + I(p, 9) + I(p, 10) + I(p, 11)]/7}.$$

Figure 8A:
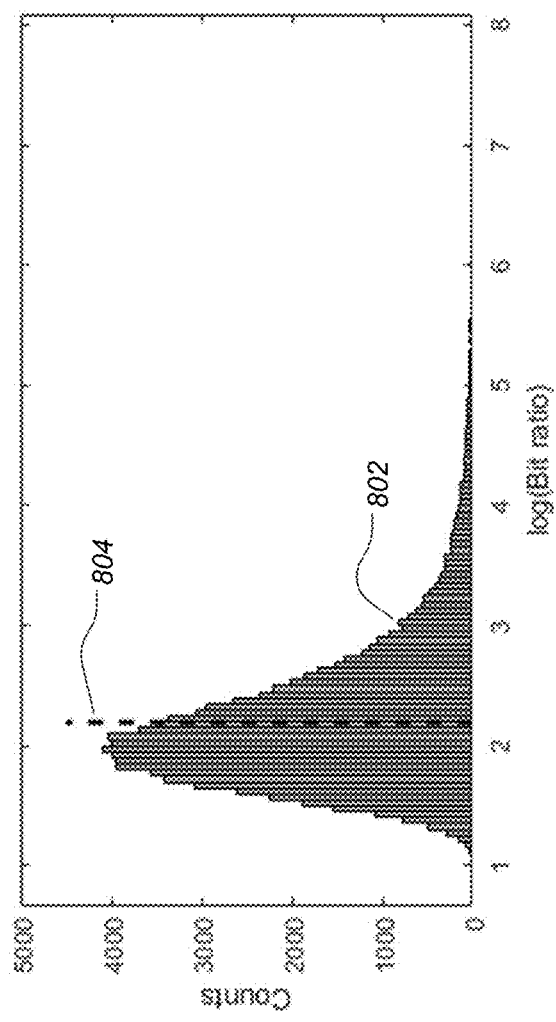
FIG. 8A is a logarithmic histogram of bit ratios for pixels identified for a sample code word.

The bit ratio BR is compared to a threshold value THBR. In some implementations, the threshold value THBR is determined empirically from prior measurements. However, in some implementations, the threshold value THBR can be calculated automatically for a particular code word based on the measurements obtained from the sample. FIG. 8A illustrates a logarithmic histogram 802 of bit ratios intensity values for all pixels that were tagged with a particular code word. A threshold value 804 is calculated based on this histogram 802. For example, a default quantile, e.g., 50%, can be used to calculate an initial threshold value 802. However, the quantile can be adjusted during optimization discussed below.

Yet another technique for filtering false callouts is to reject code words where a calculated bit brightness falls below a threshold. The bit brightness is calculated as the mean of the intensity values from the image word for layers that are supposed to be on (as determined from the code word). For example, for the code word 730 shown in FIG. 7, the bits corresponding to columns 3-6 and 12-14 are on. Thus, assuming this code word is selected as the best match for a pixel p, the bit brightness BB can be calculated as $$BB=[I(p,3)+I(p,4)+I(p,5)+I(p,6)+I(p,12)+I(p,13)+I(p,14)]/7$$

Figure 8B:
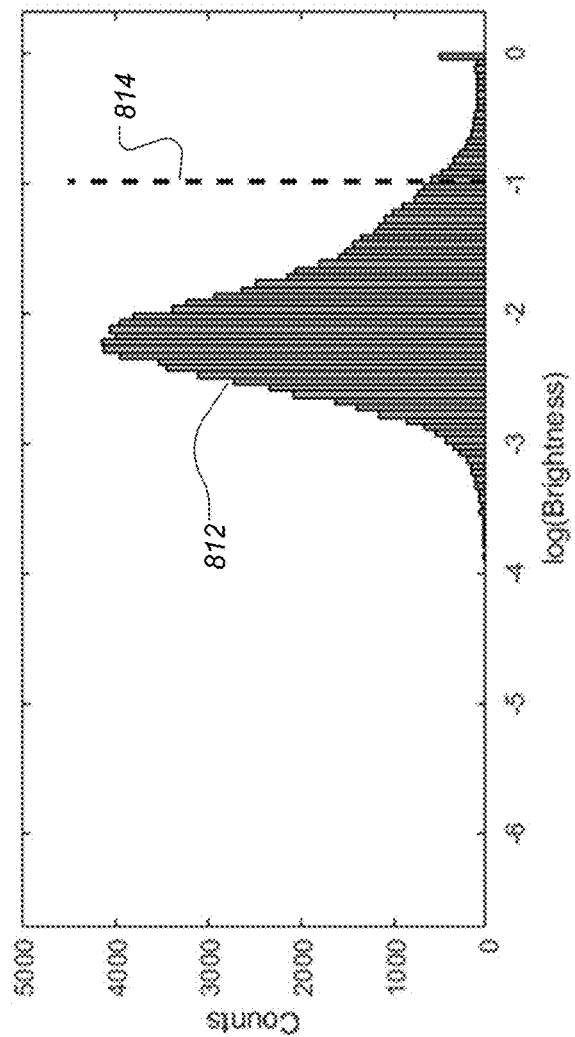
FIG. 8B is a logarithmic histogram of brightness for pixels identified for a sample code word.

The bit brightness BB is compared to a threshold value THBB. In some implementations, the threshold value THBB is determined empirically from prior measurements. However, in some implementations, the threshold value THBB can be calculated automatically for a particular code word based on the measurements obtained from the sample. FIG. 8B illustrates a logarithmic histogram 812 of bit brightness values for all pixels that were tagged with a particular code word. A threshold value 814 is calculated based on this histogram 812. For example, a default quantile, e.g., 80% or 90%, can be used to calculate an initial threshold value 814. However, the quantile can be adjusted during optimization discussed below.

Returning to FIG. 2, the data processing apparatus can now perform optimization and re-decoding (step 212). The optimization can include machine-learning based optimization of the decoding parameters, followed by returning to step 210 with updated decoding parameters in order to update the spatial transcriptomic analysis. This cycle can be repeated until the decoding parameters have stabilized.

The optimization of the decoding parameters will use a merit function, e.g., a FPKM/TPM correlation, spatial correlation, or confidence ratio. Parameters that can be included as variables in the merit function include the shape (e.g., start and end of frequency range, etc.) of the filters used to remove cellular background, the numerical aperture value for the point spread function used to sharpen the RNA spots, the quantile boundary Q used in normalization of the FOV, the bit ratio threshold THBR, the bit brightness threshold THBB (or the quantiles used to determine the bit ratio threshold THBR and bit brightness threshold THBB), and/or the maximum distance $D1_{MAX}$ at which at which a pixel word can be considered to match a code word.

This merit function may be an effectively discontinuous function, so a conventional gradient following algorithm may be insufficient to identify the optimal parameter values. A machine learning model can be used to converge on parameter values.

Next, the data processing apparatus can perform unification of the parameter values across all FOVs. Because each FOV is processed individually, each field can experience different normalization, thresholding, and filtering setting. As a result, a high contrast image can result in a histogram with variation that causes false positive callouts in quiet areas. The result of unification is that all FOVs use the same parameter values. This can significantly remove callouts from background noise in quiet area, and can provide a clear and unbiased spatial pattern in large sample area.

A variety of approaches are possible to select a parameter value that will be used across all FOVs. One option is to simply pick a predetermined FOV, e.g., the first measured FOV or a FOV near the center of the sample, and use the parameter value for that predetermined FOV. Another option is to average the values for the parameter across multiple FOV and then use the averaged value. Another option is to determine which FOV resulted in the best fit between its pixel words and tagged code words. For example, a FOV with the smallest average distance d(p,b1) between the tagged code words and the pixel words for those code words can be determined and then selected.

Alternatively, unification can be performed before the spatial transcriptomic analysis, e.g., between steps 208 and 210. In this case, the unification would be performed for parameters selected before step 210, e.g., parameters used in steps 204 or 206, but not for the parameters in steps 210 and 212.

Figure 9:
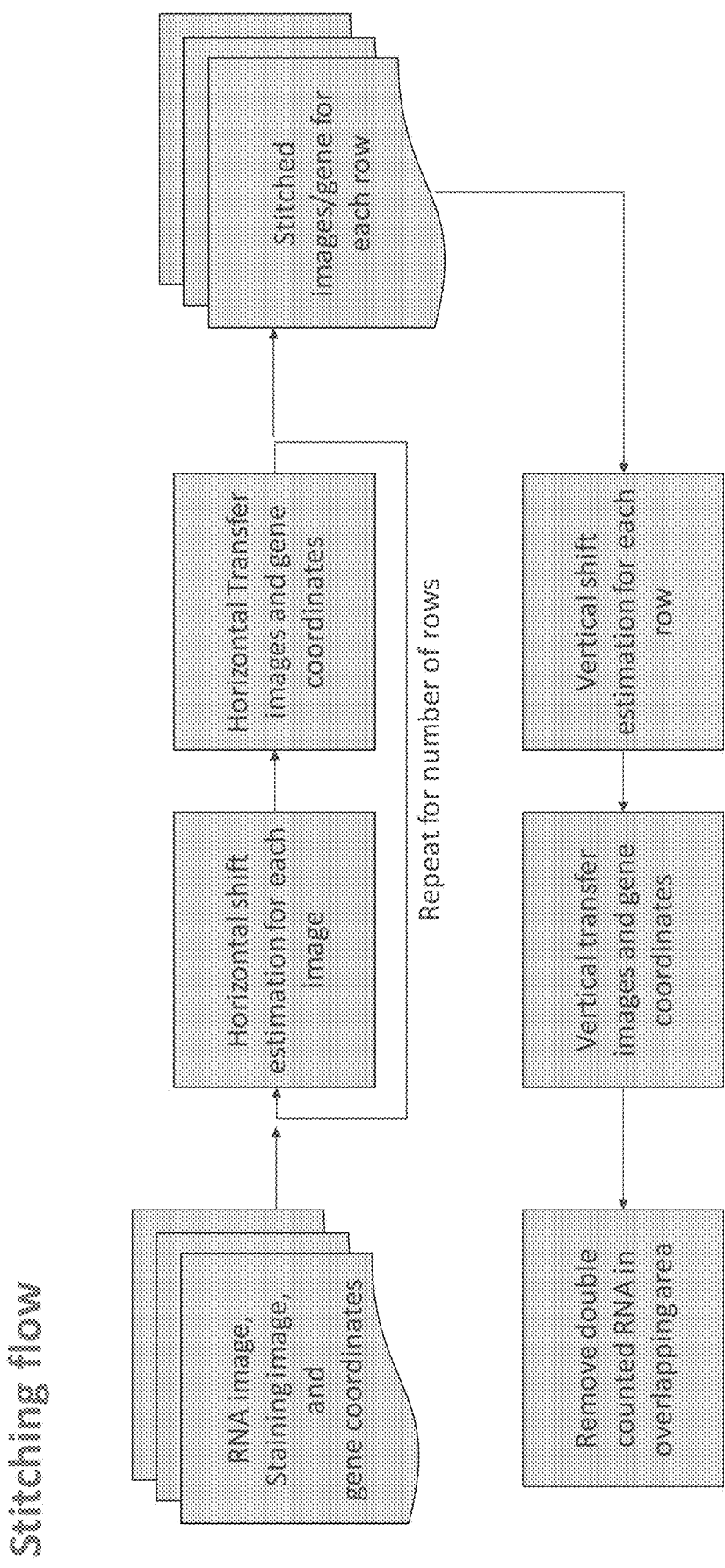
FIG. 9 is a flow chart of a method of stitching.

The data processing apparatus can now perform stitching and segmentation (step 214). Stitching combines multiple FOV into a single image. Stitching can be performed using a variety of techniques. Referring to FIG. 9, one approach is, for each row of FOV that together will form the combined image of the sample and each FOV within the row, determine a horizontal shift for each FOV. Once the horizontal shifting is calculated, a vertical shift is calculated for each row of FOV. The horizontal and vertical shifts can be calculated based on cross-correlation, e.g., phase correlation. With the horizontal and vertical shift for each FOV, a single combined image can be generated, and gene coordinates can be transferred to the combined image based on the horizontal and vertical shift.

An indication that a gene is expressed at a certain coordinate in the combined fluorescence image (as determined from the coordinate in the FOV and the horizontal and vertical shift for that FOV) can be added, e.g., as metadata. This indication can be termed a "callout."

The stain images, e.g., the DAPI images, can be stitched together using the technique discussed with respect to FIG. 9 to generate a combined stain image. In some implementations, it is not necessary to create a combined fluorescence image from the collected fluorescence images; once the horizontal and vertical shift for each FOV is determined, the gene coordinates within the combined stain image can be calculated. The stain image can be registered to the collected fluorescent image(s). An indication that a gene is expressed at a certain coordinate in the combined stain image (as determined from the coordinate in the FOV and the horizontal and vertical shift for that FOV) can be added, e.g., as metadata, to provide a callout.

A potential problem remains in the stitched image. In particular, some genes may be double-counted in the overlapping area. To remove double-counting, a distance, e.g., Euclidean distance, can be calculated between each pixel tagged as expressing a gene and other nearby pixels tagged as expressing the same gene. One of the callouts can be removed if the distance is below a threshold value. More complex techniques can be used if a cluster of pixels are tagged as expressing a gene.

Segmentation of the combined image, e.g., the image of the stained cell, into regions corresponding to cells can be performed using various known techniques. Segmentation is typically performed after stitching of the images, but can occur before or after callouts are added to the combined image.

The segmented image with callouts indicating positions of gene expression, can now be stored and presented to a user, e.g., on a visual display, for analysis.

Although the discussion above assumes that a single z-axis image is used in for each FOV, this is not required. Images from different z-axis positions can be processed separately; effectively the different z-axis positions provide a new set of FOVs.

As noted above, one problem is that the data processing, including the image processing steps, is computationally demanding and can require a significant amount of time. One issue is that in conventional techniques, all images are acquired before the image processing commences. However, it is possible to perform on-the-fly image processing as the images are received.

Figure 10:
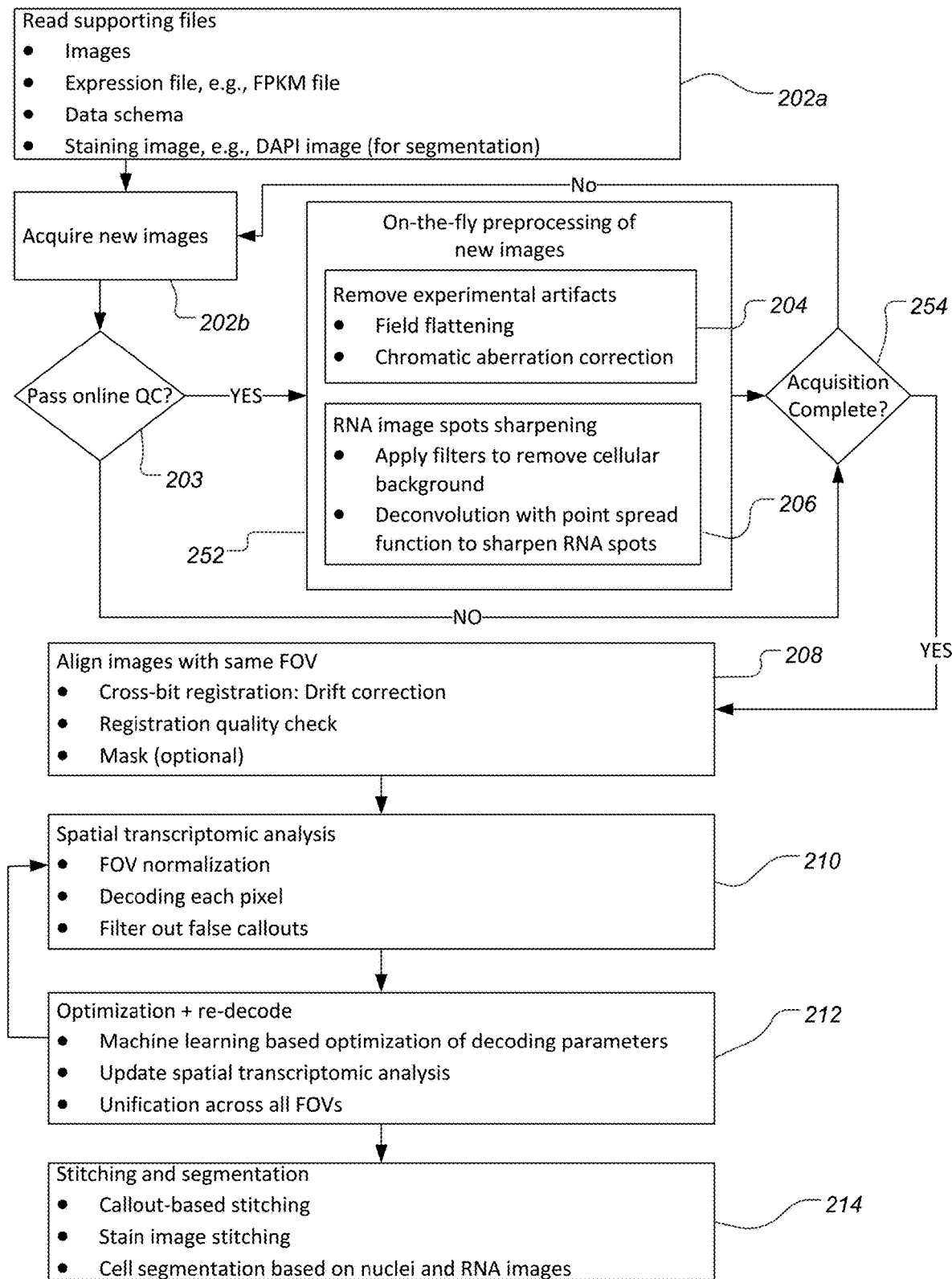
FIG. 10 is a flow chart of another implementation of a method of data processing in which image processing is performed on-the-fly.

FIG. 10 illustrates a modified data processing method in which image processing is performed on-the-fly. Steps that are not specifically discussed can be performed in a manner similar to the method of FIG. 2. Initially, the data processing system can receive the supporting files (step 202a), although this step could be postponed until after image acquisition. It may be necessary for some files, e.g., the data schema, to be loaded to the data processing system for the image processing to be performed.

The apparatus begins the process of acquiring new images (step 202b), e.g., stepping through the loops to adjust the z-axis, color channel, lateral position, and reagent, and acquiring an image at each combination of possible values for these parameters.

As each image is acquired, a quality control (QC) test is performed to determine whether the image is of sufficient quality to be pre-processed (step 203). If it is, on-the-fly pre-processing of the acquired image is performed (step 252). In this context, "on-the-fly" indicates that the processing of one image can be performed in parallel with acquisition of subsequent images. The on-the-fly pre-processing can include the removing the experimental artifacts (step 204) and RNA image spot sharpening (step 206). It may be noted that since these image preprocessing steps are performed individually for each image, and do not depend on other images in the same FOV or images for other FOV, shifting processing in this manner does not adversely impact the quality of processing. In general, significant computational load can be shifted to times when the reagent is being changed. As a result, overall time from loading of the sample into the flow cell to receiving the segmented image with callouts is significantly reduced, which can significantly improve throughput and speed research.

In some implementations, the images are pre-processed in "real time," i.e., processing of one image is performed in parallel with collection of a subsequent image by the apparatus and completed before a subsequent image is received at the data processing system.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer program product for acquiring spatial transcriptomic information, the computer program product comprising a non-transitory computer readable media having instructions to cause one or more processors to:
   receive a plurality of images of a sample, the plurality of images representing a common field of view;
   perform registration of the plurality of images to generate a plurality of registered images;
   for each pixel of a plurality of pixels of the registered images, decode the pixel by identifying a code word from a plurality of code words in a code book that provides a best match to data values in the plurality of registered images for the pixel; and
   for each code word identified as a best match for one or more pixels and each pixel of the one or more pixels, determine whether a bit ratio for an image word for the pixel meets a threshold for the code word, the image word being formed from the data values in the plurality of registered images for the pixel; and
   for at least one pixel that is determined to meet the threshold determine a gene associated with the code word and store an indication that the gene is expressed at the pixel, and screen pixels for which the bit ratio does not meet the threshold.

2. The computer program product of claim 1, wherein the code word comprises a sequence of code values and the image word comprises a sequence of data values with each data value in the sequence having a corresponding code value in the sequence of code values.

3. The computer program product of claim 2, wherein the instructions to determine the bit ratio comprise instructions to determine which code values in the code word indicate an on status and which code values in the code word indicate an "off" status.

4. The computer program product of claim 3, wherein the instructions to determine the bit ratio comprise instructions to determine a first average of data values in the image word that correspond to code values in the code word that indicate an on status.

5. The computer program product of claim 4, wherein the instructions to determine the bit ratio comprise instructions to determine a second average of data values in the image word that correspond to code values in the code word that indicate an off status.

6. The computer program product of claim 5, wherein the instructions to determine the bit ratio comprise instructions to divide the first average by the second average.

7. The computer program product of claim 1, comprising instructions to determine the threshold by determining a value at a first quantile limit in a histogram of bit values from the plurality of images of the sample.

8. The computer program product of claim 7, wherein the quantile limit has a default value.

9. The computer program product of claim 8, comprising instructions to, after determining the threshold, determine an updated threshold by determining a value at different second quantile limit in the histogram of bit values from the plurality of images of the sample.

10. A fluorescent in-situ hybridization imaging system, comprising:
   a flow cell to contain a sample to be exposed to fluorescent probes in a reagent;
   a valve to control flow from one of a plurality of reagent sources the flow cell;
   a pump to cause fluid flow through the flow cell;
   a fluorescence microscope including a variable frequency excitation light source and a camera positioned to receive fluorescently emitted light from the sample; and
   a control system configured to
      receive a plurality of images of the sample from the fluorescence microscope, the plurality of images representing a common field of view,
      perform registration of the plurality of images to generate a plurality of registered images,
      for each pixel of a plurality of pixels of the registered images, decode the pixel by identifying a code word from a plurality of code words in a code book that provides a best match to data values in the plurality of registered images for the pixel,
      for each code word identified as a best match for one or more pixels and each pixel of the one or more pixels, determine whether a bit ratio for an image word for the pixel meets a threshold for the code word, the image word being formed from the data values in the plurality of registered images for the pixel, and
      for at least one pixel that is determined to meet the threshold determine a gene associated with the code word and store an indication that the gene is expressed at the pixel, and screen pixels for which the bit ratio does not meet the threshold.

11. The system of claim 10, wherein the code word comprises a sequence of code values and the image word comprises a sequence of data values with each data value in the sequence having a corresponding code value in the sequence of code values.

12. The system of claim 11, wherein the control system is configured to determine the bit ratio by determining which code values in the code word indicate an on status and which code values in the code word indicate an "off" status.

13. The system of claim 12, wherein the control system is configured to determine a first average of data values in the image word that correspond to code values in the code word that indicate an on status.

14. The system of claim 13, wherein the control system is configured to determine a second average of data values in the image word that correspond to code values in the code word that indicate an off status.

15. The system of claim 14, wherein the control system is configured to determine the bit ratio by dividing the first average by the second average.

16. The system of claim 10, wherein the control system is configured to determine a value at a first quantile limit in a histogram of bit values from the plurality of images of the sample.

17. The system of claim 16, wherein the quantile limit has a default value.

18. The system of claim 17, wherein the control system is configured to, after determining the threshold, determine an updated threshold by determining a value at different second quantile limit in the histogram of bit values from the plurality of images of the sample.

* * * * *